US009410211B2

(12) United States Patent
Stevens

(10) Patent No.: US 9,410,211 B2
(45) Date of Patent: Aug. 9, 2016

(54) GARDNERELLA VAGINALIS ASSAY

(75) Inventor: Jason P. Stevens, Owings Mills, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 303 days.

(21) Appl. No.: 13/882,907

(22) PCT Filed: Oct. 28, 2011

(86) PCT No.: PCT/US2011/058255
§ 371 (c)(1),
(2), (4) Date: Jul. 8, 2013

(87) PCT Pub. No.: WO2012/061225
PCT Pub. Date: May 10, 2012

(65) Prior Publication Data
US 2014/0030710 A1 Jan. 30, 2014

Related U.S. Application Data

(60) Provisional application No. 61/408,840, filed on Nov. 1, 2010.

(51) Int. Cl.
C12Q 1/68 (2006.01)
C12P 19/34 (2006.01)

(52) U.S. Cl.
CPC .................................... C12Q 1/689 (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,102,784 A | 4/1992 | George, Jr. | |
| 5,130,238 A | 7/1992 | Malek et al. | |
| 5,270,184 A | 12/1993 | Walker et al. | |
| 5,427,930 A | 6/1995 | Birkenmeyer et al. | |
| 5,455,166 A | 10/1995 | Walker | |
| 5,648,211 A | 7/1997 | Fraiser et al. | |
| 5,712,124 A | 1/1998 | Walker | |
| 5,744,311 A | 4/1998 | Fraiser et al. | |
| 5,814,490 A | 9/1998 | Spears | |
| 5,928,869 A | 7/1999 | Nadeau et al. | |
| 5,962,273 A | 10/1999 | Durmowicz et al. | |
| 6,316,200 B1 | 11/2001 | Nadeau et al. | |
| 6,379,888 B1 | 4/2002 | Nadeau et al. | |
| 2010/0075306 A1 | 3/2010 | Bretelle et al. | |
| 2010/0162442 A1 | 6/2010 | Souza et al. | |
| 2011/0020355 A1 | 1/2011 | Ratner | |

FOREIGN PATENT DOCUMENTS

| | | |
|---|---|---|
| EP | 0624643 A2 | 11/1994 |
| EP | 0678582 A1 | 10/1995 |
| EP | 0684315 A1 | 11/1995 |
| JP | 2003511015 A | 3/2003 |
| WO | 9010064 A1 | 9/1990 |
| WO | 9103573 A1 | 3/1991 |
| WO | 2009117373 A2 | 9/2009 |
| WO | 2010095917 A1 | 8/2010 |

OTHER PUBLICATIONS

Lowe et al. A computer program for selection of oligonucleotide primers for polymerase chain reactions. Nucleic Acids Research (1990) vol. 18, No. 7, 1757-1761.*
Menard et al. Molecular quantification of Gardnerella vaginalis and Atopobium vaginae loads to predict bacterial vaginosis. Clinical Infectious Diseases (2008) 47:33-43.*
Cuaci S, et al . "Pore forming and haemolytic properties of the Gardnerella vaginalis cytolysin," Mole. Microbio. 9(6): pp. 1143-1155 (1993).
Gelber S., et al . "Functional and Phylogenetic Characterization of Vaginolysin, the Human Specific Cytolysin from Gardnerella vaginalis" J. Bacteriol. 190(11) :3896 3903 (2008).
Gelber, Se. etal. 'Functional and phylogenetic characterization of Vaginolysin, the human-specific cytolysin from Gardnerella vaginal is', J. Bacteriol,. Apr. 4, 2008, vol. 190, No. 11, pp. 3896-3903.
Guatelli et al., "Isothermal, in vitro amplification of nucleic acids by a multienzyme reaction modeled after retroviral replication", Proc. Nat'l Acad. Sci. USA, vol. 87, pp. 1874-1878, Mar. 1990.
International Search Report and Written Opinion for Application No. PCT/US2011/058255 dated May 15, 2012.
Kretzschmar U, et al . Purification and Characterization of Gardnerella vaginalis Hemolysin Curr. Microbiol., vol. 23(1), pp. 7-13, 1991.
Kwoh et al., "Transcription-based amplification system and detection of amplified human immunodeficiency virus type 1 with a bead-based sandwich hybridization format", Proc. Nat'l Acad. Sci. USA, vol. 86, pp. 1173-1177, Feb. 1989.
Little et al., "Molecular Diagnostics and Genetics", Clinical Chemistry 45 ( 6 ): 777-784 (1999).
Lizardi et al., "Exponential Amplification of Recombinant · RNA Hybridization Probes" BioTechnology, vol. 6, pp. 1197-1202, 1988.
Lizardi et al., "Mutation detection and single-molecule counting using isothermal rolling-circle amplification" Nat Genet, vol. 19, pp. 225-232, Jul. 1998.
Database EMBL [Online] Jun. 28, 2011, "JP 2006507841-A/11 08135: Functional and Hyperfunctional siRNA.", retrieved from EBI accession No. EM PAT:GB545726 Database accession No. GB545726.
Database EMBL [Online] Jun. 28, 2011, " JP2006507841-A/ 1497073: Functional and Hyperfunctional siRNA.", retrieved from EBI accession No. EM PAT:GB934664 Database accession No. GB934664.
Database Geneseq [Online] Oct. 15, 1997, "Fibrillin 1 Fbn1 gene primer B2.", retrieved from EBI accession No. GSN :AAT51773 Database accession No. AAT51773.

(Continued)

Primary Examiner — David Thomas
(74) Attorney, Agent, or Firm — Lerner, David, Littenberg, Krumholz & Mentlik, LLP

(57) ABSTRACT

The present invention relates to nucleic acid amplification assays for the detection of nucleic acid sequences of Gardnerella vaginalis. The present invention provides oligonucleotides that are complementary or that anneal to nucleic acid sequences of the vly gene of GV. The present invention also provides internal amplification controls (IACs) that can be used in nucleic acid amplification reactions.

18 Claims, 4 Drawing Sheets

(56) References Cited

OTHER PUBLICATIONS

Database Geneseq [Online] Aug. 19, 2010, "Sugarcane assembled sequence specific real-time PCR primer, SEQ ID 400.", retrieved from EBI accession No. GSN :AYD77201 Database accession No. AYD77201.

Database Geneseq [Online] Feb. 21, 2008, "Saccharum stree related gene RT-PCR primer, SEQ ID 400.", retrieved from EBI accession No. GSN:AOF47809 Database accession No. OF47809.

Database Geneseq [Online] Jan. 26, 1996, "Self splicing intron amplification primer oligo-4445.", retrieved from EBI accession No. GSN :AAQ94927 Database accession No. AAQ94927.

Database Geneseq [Online] Mar. 8, 2007, "Bovine FABP 4 gene, SNP at 7516 #1.", retrieved from EBI accession No. GSN:AEN60405 Database accession No. AEN60405.

Database Geneseq [Online] Jul. 9, 2009, "Human LOC643997 gene short interfering RNA target sequence.", retrieved from EBI accession No. GSN:AWW33851 Database accession No. AWW33851.

Extended European Search Report for Application No. EP 11838580 dated Apr. 2, 2014.

Randis Tara M et al: "Antibody-Based Detection and Inhibition of Vaginolysin, the Gardnerella vaginalis Cytolysin", PLOS ONE, Public Library of Science, US, vol. 4, No. 4, Apr. 16, 2009, p. e5207, XP009128317, ISSN: 1932-6203, DOI: 10.1371/JOURNAL.PONE. 0005207, the whole document.

\* cited by examiner

Positions of the Annealing Regions of Oligonucleotides that Form the GV SDA Assay Bumper: GV vly LB7 nt 326-357    5'- G C C A A C G A T C G C T A T A C C A G G T G C T C T T T T C C G T G
              3'- C G G T T G C T A G C G A T A T G G T C C A C G A G A A A A G G C A C

Primer: GV vly LP6 nt 358-407    C T G A T A A A G A A T T T G A T G G A C A A T A T G C C A A G C C T G A T T T C
              G A C T A T T T C T T A A A C T A C C T G T T A T A C G G T T C G G A C T A A A G

Detector: GV vly DT5 nt 408-447    T G C A A A C C G C G C T C C A A T A A C G T T G A G C G G T T G A T T T G C C G
              A C G T T T G G C G C G A G G T T A T T G C A A C T C G C C A A C T A A A C G G C

Bumper: GV vly R38 nt 448-487    G G A T T C C A C G G C C G G C G A A A A G T G C T G T A A C T G T T C A G C G C C
              C C T A A G G T G C C G G C C G C T T T T C A C G A C A T T G A C A A G T C G C G G nt 488-523    C A A C C A A G A G A G C T C T G T A A C T T C C G G C A G T G A A C G G C T -3'
              G T T G G T T C T C T C G A G A C A T T G A A G G C C G T C A C T T G C C G A -5'

FIG. 3

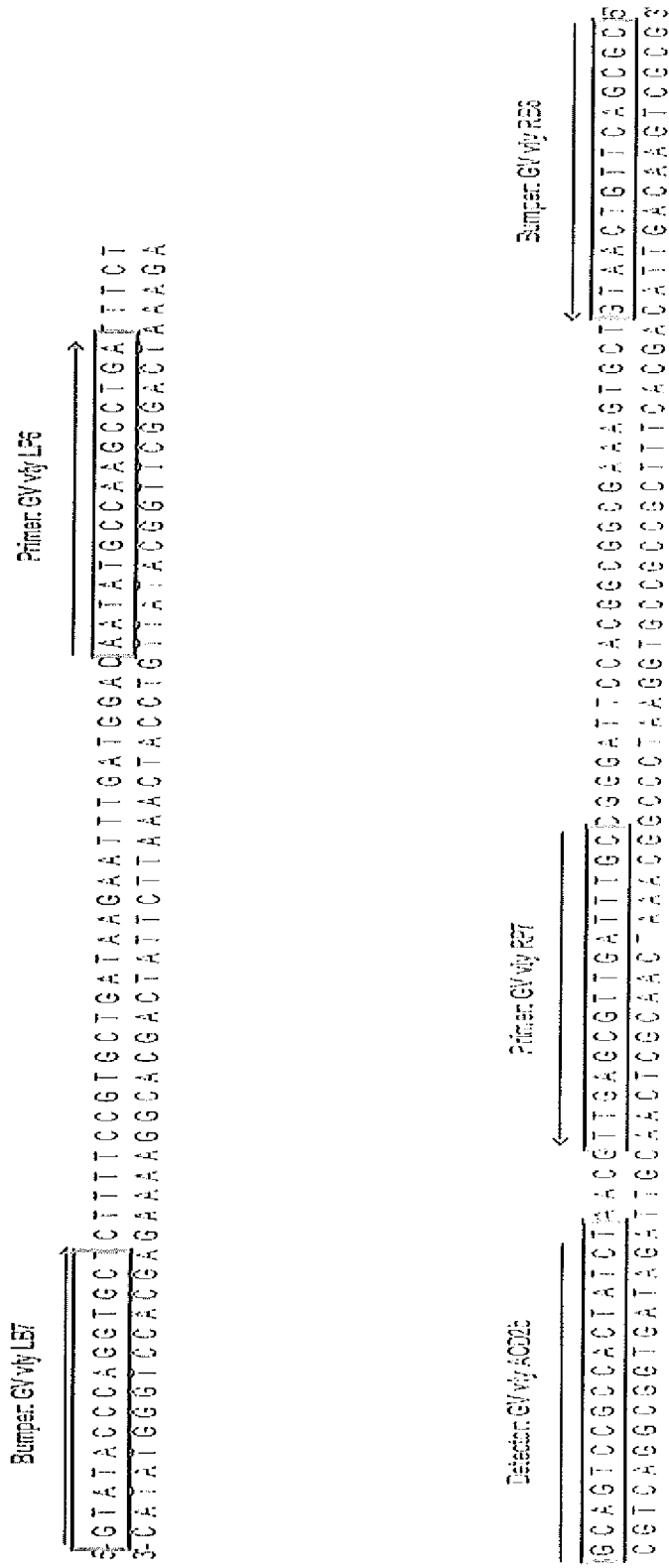

SEQUENCE LISTING

```
<160> NUMBER OF SEQ ID NOS: 25

<210> SEQ ID NO 1
<211> LENGTH: 1551
<212> TYPE: DNA
<213> ORGANISM: Gardnerella vaginalis
<220> FEATURE:
<221> NAME/KEY: source
<222> LOCATION: (1)..(1551)
<223> OTHER INFORMATION: strain 14018 of GV vly gene
<300> PUBLICATION INFORMATION:
<308> DATABASE ACCESSION NUMBER: NCBI GenBank Accession No. EU522486
<309> DATABASE ENTRY DATE: 2008-05-19
<313> RELEVANT RESIDUES IN SEQ ID NO: (1)..(1551)

<400> SEQUENCE: 1
atgaagagta caaagttcta ccgtaatgca gcaatgttgc tcctcgcggg cgcaactatt      60
gttccacaat gcttagcagc accagcaatg gccgctcctt ccgctaagga ttctgaacca     120
gctacatctt gcgcagctaa gaaagactcg ttgaataatt atttgtggga tttgcaatac     180
gataaaacaa acattctcgc ccgtcatggc gaaaccattg agaacaaatt ctccagcgac     240
agcttcaaca agaacggtga attcgttgtt gttgagcatc agaagaagaa catcaccaat     300
acaacttcaa atttgtcggt tacttccgcc aacgatgatc gcgtataccc aggtgctctt     360
ttccgtgctg ataagaattt gatggacaat atgccaagcc tgatttctgc aaaccgcgct     420
```

```
ccaataacgt tgagcgttga tttgccggga ttccacggcg gcgaaagtgc tgtaactgtt      480
cagcgcccaa ccaagagctc tgtaacttcc gcagtgaacg gcttagtttc taagtggaat      540
gcacaatatg gagcaagtca tcatgttgca gctcgcatgc agtacgattc tgcaagcgca      600
caaagcatga accagctcaa ggctaagttt ggtgctgatt ttgccaagat tggtgttccg      660
ctgaagattg atttcgatgc agtacacaag ggtgagaagc agactcaaat tgtgaacttc      720
aagcaaactt actaccacgt aagcgttgat gcaccagata gcccagcaga tttctttgct      780
ccttgcacta cgccagacag cttgaagaac cgtggcgttg acaacaagcg cccaccagtt      840
tacgtgtcaa acgtagctta tggtcgctca atgtacgtaa agttcgatac caccagcaag      900
agcactgatt tccaggctgc ggtagaagca gcaattaagg gcgtagaaat caagccaaac      960
accgaattcc atcgcattct ccagaatact tctgttactg cagtgattct tggtggcagc     1020
gctaatggtg cagctaaagt tattacaggc aatatcgata cgcttaaggc tttgattcag     1080
gaaggtgcaa atttgagcac ctctagccca gcggttccaa ttgcatacac cacttccttc     1140
gtcaaggata acgaagtagc aactttgcaa tccaacagcg attatattga aacgaaggtt     1200
tcttcttatc gcaatggcta cttgactttg gaccaccgtg gagcttatgt agctcgctac     1260
tacatctact gggatgagta cggcaccgaa attgacggca ctccttacgt gcgttctcgc     1320
gcttgggaag gcaatggtaa gtatcgtaca gctcacttca acaccactat tcagttcaaa     1380
ggaaatgtac gcaatctacg aatcaagttg gttgaaaaga ctggtttggt ttgggaacca     1440
tggcgcacag tatatgaccg ttctgatttg ccactagttc gtcagcgtac tattagcaac     1500
tggggcacaa ccttgtggcc tcgcgttgct gaaactgtaa agaacgactg a               1551

<210> SEQ ID NO 2
<211> LENGTH: 1554
<212> TYPE: DNA
<213> ORGANISM: Gardnerella vaginalis
<220> FEATURE:
<221> NAME/KEY: source
<222> LOCATION: (1)..(1554)
<223> OTHER INFORMATION: T10 clone
<300> PUBLICATION INFORMATION:
<308> DATABASE ACCESSION NUMBER: NCBI GenBank Accession No. EU697811
<309> DATABASE ENTRY DATE: 2010-05-11
<313> RELEVANT RESIDUES IN SEQ ID NO: (1)..(1554)

<400> SEQUENCE: 2
catatgaata acacaaagtt ctaccgtaat gcagcaatgt tgctcctcgc gggcgcaact       60
attattccac aatgcttagc agcaccagca atggccgctc ctgcagctaa ggattctgag      120
ccaaccgcat cttgcgcagc caagaaggac tcgttgaata ttatttgtg ggatttgcaa       180 tacgataaaa caaacattct cgcccgtcat ggcgaaacca ttgacaacaa attctctagc      240
gatagcttca acaagggcga tgaattcgtt gttgttgagc atcagaagaa gaacatcaca      300
aatacaactt caaacttgtc ggttacttcc gccaacgatg atcgcgtata cccaggtgct      360
cttttccgcg ctgaccagaa tttgatggac aatatgccaa gcctgatttc cgcaaaccgc      420
gctccaatca cgttgagcgt tgatttgcca ggcttccacg gcggcgaaag tgctgtaact      480
gttcagcgcc caaccaagag ctctgtaact tccgcagtga acggcttagt ttccaagtgg      540
aatgcacagt acgctgcaag ccatcatgtt gcagctcgca tgcagtacga ttctgcaagc      600
gcacaaagca tgaaccagct caaggcaaag tttggtgctg atttcgccaa gattggcgtt      660
ccgctgaaga ttgatttcga cgctgtgcac aagggcgaaa agcagactca aattgtgaac      720
ttcaagcaga cctactacac cgtaagtgtt gatgctccag atagcccagc tgacttcttc      780
```

```
gcaccatgca ctacgccaga aagcttgaag agccgcggag tagacagcaa gcgtccgcca    840
gtatatgtgt ccaacgtagc ttacggccgt tcaatgtacg taaagttcga cacccgcagc    900
aagagcaccg atttccaggc tgctgttgaa gctgcaatca agggtgttga aatcaagcca    960
aataccgagt tccaccgcat tttgcagaac acttctgtaa ctgctgtaat tctcggcggc   1020
agcgcagacg gtgcagccaa ggttattacc ggcaacgtcg acacgttgaa ggctttgatt   1080
caagaaggcg caaatttgag cacctccagc ccagcagttc cagttgctta caccacttcc   1140
ttcgccaagg ataacgaagt agcaactttg caaaccaata gcgattacgt tgaaaccaag   1200
gtttcttcct accgcgacgg ctacttgact ttggatcacc gtggagctta cgtagctcgc   1260
tactacatct actgggatga gtacggcacc gaaattgacg gcactcctta cgtgcgttct   1320
cgcgcttggg aaggcaatgg caagtatcgt acagctcact tcaacaccac tattcagttc   1380
aaaggaaatg tacacaatct acgaaccaag ctggttgaaa agactggctt agtttgggaa   1440
ccatggcgta cagtatatga ccgttccgat ttgccactgg ttcgccagcg cacaatcaag   1500
aactggggca aaccttgtg gccacgcgtt gctgaaactg taaagaacga ctaa           1554
```

```
<210> SEQ ID NO 3
<211> LENGTH: 16
<212> TYPE: DNA
<213> ORGANISM: Artificial Sequence
<220> FEATURE:
<223> OTHER INFORMATION: Synthetic Primer

<400> SEQUENCE: 3
aatatgccaa gcctga                                                      16

<210> SEQ ID NO 4
<211> LENGTH: 16
<212> TYPE: DNA
<213> ORGANISM: Artificial Sequence
<220> FEATURE:
<223> OTHER INFORMATION: Synthetic Primer

<400> SEQUENCE: 4
gcaaatcaac gctcaa                                                      16

<210> SEQ ID NO 5
<211> LENGTH: 16
<212> TYPE: DNA
<213> ORGANISM: Artificial Sequence
<220> FEATURE:
<223> OTHER INFORMATION: Synthetic Probe

<400> SEQUENCE: 5
gcaaaccgcg ctccaa                                                      16

<210> SEQ ID NO 6
<211> LENGTH: 15
<212> TYPE: DNA
<213> ORGANISM: Artificial Sequence
<220> FEATURE:
<223> OTHER INFORMATION: Synthetic Primer

<400> SEQUENCE: 6
gtatacccag gtgct                                                       15

<210> SEQ ID NO 7
<211> LENGTH: 15
<212> TYPE: DNA
```

```
<213> ORGANISM: Artificial Sequence
<220> FEATURE:
<223> OTHER INFORMATION: Synthetic Primer

<400> SEQUENCE: 7
gcgctgaaca gttac                                                    15

<210> SEQ ID NO 8
<211> LENGTH: 18
<212> TYPE: DNA
<213> ORGANISM: Artificial Sequence
<220> FEATURE:
<223> OTHER INFORMATION: Synthetic Primer

<400> SEQUENCE: 8
ggcggcgaaa gtgctgta                                                 18

<210> SEQ ID NO 9
<211> LENGTH: 19
<212> TYPE: DNA
<213> ORGANISM: Artificial Sequence
<220> FEATURE:
<223> OTHER INFORMATION: Synthetic Primer

<400> SEQUENCE: 9
agccgttcac tgcggaagt                                                19

<210> SEQ ID NO 10
<211> LENGTH: 25
<212> TYPE: DNA
<213> ORGANISM: Artificial Sequence
<220> FEATURE:
<223> OTHER INFORMATION: Synthetic Probe

<400> SEQUENCE: 10
ttcagcgccc aaccaagagc tctgt                                         25

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
gccaacgatg atcgcgtat                                                19

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
caggcttggc atattgtcca t                                             21

<210> SEQ ID NO 13
<211> LENGTH: 24
<212> TYPE: DNA
<213> ORGANISM: Artificial Sequence
<220> FEATURE:
<223> OTHER INFORMATION: Synthetic Probe

<400> SEQUENCE: 13
cccaggtgct cttttcgctg ctga                                          24
```

<210> SEQ ID NO 14
<211> LENGTH: 15
<212> TYPE: DNA
<213> ORGANISM: Artificial Sequence
<220> FEATURE:
<223> OTHER INFORMATION: Synthetic Primer

<400> SEQUENCE: 14
gtatacccag gtgct                                                        15

<210> SEQ ID NO 15
<211> LENGTH: 40
<212> TYPE: DNA
<213> ORGANISM: Artificial Sequence
<220> FEATURE:
<223> OTHER INFORMATION: Synthetic Primer

<400> SEQUENCE: 15
accgcatcga atgcatgtct cgggaatatg ccaagcctga                             40

<210> SEQ ID NO 16
<211> LENGTH: 15
<212> TYPE: DNA
<213> ORGANISM: Artificial Sequence
<220> FEATURE:
<223> OTHER INFORMATION: Synthetic Primer

<400> SEQUENCE: 16
gcgctgaaca gttac                                                        15

<210> SEQ ID NO 17
<211> LENGTH: 40
<212> TYPE: DNA
<213> ORGANISM: Artificial Sequence
<220> FEATURE:
<223> OTHER INFORMATION: Synthetic Primer

<400> SEQUENCE: 17
cgattccgct ccagacttct cggggcaaat caacgctcaa                             40

<210> SEQ ID NO 18
<211> LENGTH: 25
<212> TYPE: DNA
<213> ORGANISM: Artificial Sequence
<220> FEATURE:
<223> OTHER INFORMATION: Synthetic Probe

<400> SEQUENCE: 18
tccccgagtg caaaccgcgc tccaa                                             25

<210> SEQ ID NO 19
<211> LENGTH: 144
<212> TYPE: DNA
<213> ORGANISM: Artificial Sequence
<220> FEATURE:
<223> OTHER INFORMATION: Internal Amplification Control sample

<400> SEQUENCE: 19
gtatacccag gtgctctttt ccgtgctgat aagaatttga tggacaatat gccaagcctg       60
atttctgcag tccgccacta tctaacgttg agcgttgatt tgccgggatt ccacggcggc      120
gaaagtgctg taactgttca gcgc                                             144

<210> SEQ ID NO 20

```
<211> LENGTH: 196
<212> TYPE: DNA
<213> ORGANISM: Gardnerella vaginalis

<400> SEQUENCE: 20
gccaacgatg atcgcgtata cccaggtgct cttttccgtg ctgataagaa tttgatggac      60
aatatgccaa gcctgatttc tgcaaaccgc gctccaataa cgttgagcgt tgatttgccg     120
ggattccacg gcggcgaaag tgctgtaact gttcagcgcc caaccaagag ctctgtaact     180
tccgcagtga acggct                                                    196

<210> SEQ ID NO 21
<211> LENGTH: 196
<212> TYPE: DNA
<213> ORGANISM: Gardnerella vaginalis

<400> SEQUENCE: 21
gccaacgatg atcgcgtata cccaggtgct cttttccgcg ctgaccagaa tttgatggac      60
aatatgccaa gcctgatttc cgcaaaccgc gctccaatca cgttgagcgt tgatttgcca     120
gcattccacg gcggcgaaag tgctgtaact gttcagcgcc caaccaagag ctctgtaact     180
tccgcagtga acggct                                                    196

<210> SEQ ID NO 22
<211> LENGTH: 25
<212> TYPE: DNA
<213> ORGANISM: Artificial Sequence
<220> FEATURE:
<223> OTHER INFORMATION: Synthetic Probe

<400> SEQUENCE: 22
tccccgagtg cagtccgcca ctatc                                           25

<210> SEQ ID NO 23
<211> LENGTH: 1551
<212> TYPE: DNA
<213> ORGANISM: Gardnerella vaginalis
<220> FEATURE:
<221> NAME/KEY: source
<222> LOCATION: (1)..(1551)
<223> OTHER INFORMATION: strain 14019 of GV vly gene
<300> PUBLICATION INFORMATION:
<308> DATABASE ACCESSION NUMBER: NCBI GenBank Accession No. EU522487
<309> DATABASE ENTRY DATE: 2008-05-19
<313> RELEVANT RESIDUES IN SEQ ID NO: (1)..(1551)

<400> SEQUENCE: 23
atgaagagta caaagttcta ccgtaatgca gcaatgttgc tcctcgcggg cgcaactatt      60
gttccacaat gcttagcagc accagcaatg gccgctcctt ccgctaagga ttctgaacca     120
gctacatctt gcgcagctaa gaaagactcg ttgaataatt atttgtggga tttgcaatac     180
gataaaacaa acattctcgc ccgtcatggc gaaaccattg agaacaaatt ctccagcgac     240
agcttcaaca gaacggtga attcgttgtt gttgagcatc agaagaagaa catcaccaat     300
acaacttcaa atttgtcggt tacttccgcc aacgatgatc gcgtataccc aggtgctctt     360
ttccgtgctg ataagaattt gatggacaat atgccaagcc tgatttctgc aaaccgcgct     420
ccaataacgt tgagcgttga tttgccggga ttccacggcg cgaaagtgc tgtaactgtt      480 cagcgcccaa ccaagagctc tgtaacttcc gcagtgaacg gcttagtttc taagtggaat     540
gcacaatatg gagcaagtca tcatgttgca gctcgcatgc agtacgattc tgcaagcgca     600
caaagcatga accagctcaa ggctaagttt ggtgctgatt ttgccaagat tggtgttccg     660
```

```
ctgaagattg atttcgatgc agtacacaag ggtgagaagc agactcaaat tgtgaacttc      720
aagcaaactt actacaccgt aagcgttgat gcaccagata gcccagcaga tttctttgct      780
ccttgcacta cgccagacag cttgaagaac cgtggcgttg acaacaagcg cccaccagtt      840
tacgtgtcaa acgtagctta tggtcgctca atgtacgtaa agttcgatac caccagcaag      900
agcactgatt tccaggctgc ggtagaagca gcaattaagg gcgtagaaat caagccaaac      960
accgaattcc atcgcattct ccagaatact tctgttactg cagtgattct tggtggcagc     1020
gctaatggtg cagctaaagt tattacaggc aatatcgata cgcttaaggc tttgattcag     1080
gaaggtgcaa atttgagcac ctctagccca gcggttccaa ttgcatacac cacttccttc     1140
gtcaaggata acgaagtagc aactttgcaa tccaacagcg attatattga aacgaaggtt     1200
tcttcttatc gcaatggcta cttgactttg gaccaccgtg gagcttatgt agctcgctac     1260
tacatctact gggatgagta cggcaccgaa attgacggca ctccttacgt gcgttctcgc     1320
gcttgggaag gcaatggtaa gtatcgtaca gctcacttca acaccactat tcagttcaaa     1380
ggaaatgtac gcaatctacg aatcaagttg gttgaaaaga ctggtttggt ttgggaacca     1440
tggcgcacag tatatgaccg ttctgatttg ccactagttc gtcagcgtac tattagcaac     1500
tggggcacaa ccttgtggcc tcgcgttgct gaaactgtaa agaacgactg a              1551

<210> SEQ ID NO 24
<211> LENGTH: 1551
<212> TYPE: DNA
<213> ORGANISM: Gardnerella vaginalis
<220> FEATURE:
<221> NAME/KEY: source
<222> LOCATION: (1)..(1551)
<223> OTHER INFORMATION: strain 49145 of GV vly gene
<300> PUBLICATION INFORMATION:
<308> DATABASE ACCESSION NUMBER: NCBI GenBank Accession No. EU522488
<309> DATABASE ENTRY DATE: 2008-05-19
<313> RELEVANT RESIDUES IN SEQ ID NO: (1)..(1551)

<400> SEQUENCE: 24
atgaagagta caaagttcta ccgtaatgca gcaatgttgc tcctcgcggg cgcaactatt       60
gttccacaat gcttagcagc accagcaatg gccgctcctt ccgctaagga ttctgaacca      120
gctacatctt gcgcagctaa gaaagactcg ttgaataatt atttgtggga tttgcaatac      180
gataaaacaa acattctcgc ccgtcatggc gaaaccattg agaacaaatt ctccagcgac      240
agcttcaaca gaacggtga attcgttgtt gttgagcatc agaagaagaa catcaccaat      300
acaacttcaa atttgtcggt tacttccgcc aacgatgatc gcgtataccc aggtgctctt      360
ttccgtgctg ataagaattt gatggacaat atgccaagcc tgatttctgc aaaccgcgct      420
ccaataacgt tgagcgttga tttgccggga ttccacggcg gcgaaagtgc cgtaactgtt      480
cagcgcccaa ccaagagctc tgtaacttcc gcagtgaacg gcttagtttc taagtggaat      540
gcacaatatg gagcaagtca tcatgttgca gctcgcatgc agtacgattc tgcaagcgca      600
caaagcatga accagctcaa ggctaagttt ggtgctgatt ttgccaagat tggtgttccg      660
ctgaagattg atttcgatgc agtacacaag ggtgagaagc agactcaaat tgtgaacttc      720
aagcaaactt actacaccgt aagcgttgat gcaccagata gcccagcaga tttctttgct      780
ccttgcacta cgccagacag cttgaagaac cgtggcgttg acaacaagcg cccaccagtt      840
tacgtgtcaa acgtagctta tggtcgctca atgtacgtaa agttcgatac caccagcaag      900
agcactgatt tccaggctgc agtagaagca gcaattaagg gcgtagaaat caagccaaac      960
```

| | |
|---|---|
| accgaattcc atcgcattct ccaaaatact tctgttactg cagtgattct tggtggcagc | 1020 |
| gctaatggtg cagctaaagt tattacaggc aacatcgata cgttgaaggc tttgattcag | 1080 |
| gaaggtgcaa atttgagcac ctctagccca gcagttccaa ttgcatacac cacttccttc | 1140 |
| gtcaaggata acgaagtagc aactttgcaa tccaacagcg attatattga aacgaaggtt | 1200 |
| tcctcttacc gcaatggcta cttgactttg gaccaccgtg gagcttacgt agctcgctac | 1260 |
| tacatctact gggatgagta cggcaccgaa attgacggca ctccttacgt gcgttctcgc | 1320 |
| gcttgggaag gcaatggtaa gtatcgtaca gctcacttca ataccactat tcagttcaaa | 1380 |
| ggaaatgtac gcaatctacg aatcaagttg gttgaaaaga ctggtttagt ttgggaacca | 1440 |
| tggcgcacag tatatgaccg ttctgatttg ccactagttc atcagcgtac tattagcaac | 1500 |
| tggggcacaa ccttgtggcc tcgcgttgct gaaactgtaa agaacgactg a | 1551 |

<210> SEQ ID NO 25
<211> LENGTH: 1554
<212> TYPE: DNA
<213> ORGANISM: Gardnerella vaginalis
<220> FEATURE:
<221> NAME/KEY: source
<222> LOCATION: (1)..(1554)
<223> OTHER INFORMATION: T11 clone
<300> PUBLICATION INFORMATION:
<308> DATABASE ACCESSION NUMBER: NCBI GenBank Accession No. EU697812
<309> DATABASE ENTRY DATE: 2010-05-11
<313> RELEVANT RESIDUES IN SEQ ID NO: (1)..(1554)

<400> SEQUENCE: 25

| | |
|---|---|
| catatgaata acacaaagtt ctaccgtaat gcagcaatgt tgctcctcgc gggcgcaact | 60 |
| attattccac aatgcttagc agcaccagca atggccgctc ctgcagctaa ggattctgag | 120 |
| ccaaccgcat cttgcgcagc caagaaggac tcgttgaata attatttgtg ggatttgcaa | 180 |
| tacgataaaa caaacattct cgcccgtcat ggcgaaacca ttgacaacaa attctctagc | 240 |
| gatagcttca acaagggcga tgaattcgtt gttgttgagc atcagaagaa gaacatcaca | 300 |
| aatacaactt caaacttgtc ggttacttcc gccaacgatg atcgcgtata cccaggtgct | 360 |
| cttttccgcg ctgaccagaa tttgatggac aatatgccaa gcctgatttc cgcaaaccgc | 420 |
| gctccaatca cgttgagcgt tgatttgcca ggcttccacg gcggcgaaag tgctgtaact | 480 |
| gttcagcgcc caaccaagag ctctgtaact tccgcagtga acggcttagt ttccaagtgg | 540 |
| aatgcacagt acgctgcaag ccatcatgtt gcagctcgca tgcagtacga ttctgcaagc | 600 |
| gcacaaagca tgagccagct caaggcaaag tttggtgctg atttcgccaa gattggcgtt | 660 |
| ccgctgaaga ttgatttcga cgctgtgcac aagggcgaaa agcagactca aattgtgaac | 720 |
| ttcaagcaga cctactacac cgtaagtgtt gatgctccag atagcccagc tgacttcttc | 780 |
| gcaccatgca ctacgccaga aagcttgaag agccgcggag tagacagcaa gcgtccgcca | 840 |
| gtatatgtgt ccaacgtagc ttacggccgt tcaatgtacg taaagttcga cacccgcagc | 900 |
| aagagcaccg atttccaggc tgctgttgaa gctgcaatca agggtgttga aatcaagcca | 960 |
| aataccgagt tccaccgcat tttgcagaac acttctgtaa ctgctgtaat tctcggcggc | 1020 |
| agcgcaaacg gtgcagccaa ggttattacc ggcaacgtcg acacgttgaa ggcttttgatt | 1080 |
| caagaaggcg caaatttgag cacctccagc ccagcagttc caattgctta caccacttcc | 1140 |
| ttcgtcaagg ataacgaagt agcaactttg caaaccaata gcgattacgt tgagaccaag | 1200 |
| gtttcttcct accgcgacgg ctacttgact ttggatcacc gtggagctta cgtagctcgc | 1260 |
| tactacatct actgggatga gtacggcacc gaaattgacg gcactcctta cgtgcgttct | 1320 |

```
cgcgcttggg aaggcaatgg caagtatcgt acagctcact tcaacaccac tattcagttc    1380
aaaggaaatg tacacaatct acgaatcaag ctggttgaaa agactggctt agtttgggaa    1440
ccatggcgta cagtatatga ccgttccgat ttgccactgg ttcgccagcg cacaatcaag    1500
aactggggca caaccttgtg gccacgcgtt gctgaaactg taaagaacga ctaa          1554
```

GARDNERELLA VAGINALIS ASSAY

CROSS REFERENCE TO RELATED APPLICATIONS

This application claims the benefit of the filing date of U.S. Provisional Patent Application No. 61/408,840 filed Nov. 1, 2010, the disclosure of which is hereby incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 19, 2011, is named Sequence Listing for Gardnerella vaginalis_ST25.txt and is 15.6 kilobytes in size.

FIELD OF INVENTION

The present invention relates to nucleic acid amplification methods for the detection and/or quantitation of nucleic acid sequences of *Gardnerella vaginalis* (also referred to herein as GV). The present invention provides oligonucleotides that are complementary or that anneal to nucleic acid sequences of *Gardnerella vaginalis* for the amplification and/or detection of the same. The present invention provides a strand displacement amplification (SDA) assay or a PCR assay for the amplification and/or detection of *Gardnerella vaginalis* nucleic acid sequences. The SDA assay may optionally be a diplex SDA that includes internal amplification controls (IAC).

BACKGROUND OF THE INVENTION

*Gardnerella vaginalis* (GV) is a gram-variable coccobacillus that has been discussed to be the sole causative agent of nonspecific vaginitis. Kretzschmar U, et al. "Purification and Characterization of *Gardnerella vaginalis* Hemolysin Curr. Microbiol. 23(1):7 13 (1991). Diagnosis and detection of this organism is often on the basis of the pathologic or clinical findings and may be confirmed by isolation and staining techniques. For example, in Kretzschmar et al., the basis for the detection and characterization of GV was the extracellular hemolysin produced by the organism. Gelber S., et al. "Functional and Phylogenetic Characterization of Vaginolysin, the Human Specific Cytolysin from *Gardnerella vaginalis*" J. Bacteriol. 190(11):3896 3903 (2008) identified another one of the extracellular hemolysins produced by GV as vaginolysin. Rottini, G., et al. "Identification and Partial Characterization of a Cytolytic Toxin Produced by *Gardnerella vaginalis*" Infect. and Immun. 58(11):3751 3758 (1990) identify the hemolysin produced by GV as cytolysin. The difficulties in isolating these toxins produced by GV are described in Cuaci S, et al. "Pore forming and haemolytic properties of the *Gardnerella vaginalis* cytolysin," Mole. Microbio. 9(6):1143 1155 (1993)

Much has been written about the measurement and detection of the toxins produced by GV to detect GV. However, a method for detecting GV based upon the organism itself, as opposed to the toxins it produces, continues to be sought. Thus, there is a need for an assay that decreases the possibility of false negative results.

Citation or discussion of a reference herein shall not be construed as an admission that such is prior art to the present invention.

SUMMARY OF THE INVENTION

Described herein is a method for detecting qualitatively and/or quantitatively the presence or absence of *Gardnerella vaginalis* in a sample, said method comprising: (a) amplifying the target sequence using a first amplification primer having a sequence consisting essentially of the target binding sequence of any amplification primer disclosed herein and (b) detecting the amplified target sequence. In certain embodiments, the use of a second amplification primer consisting essentially of the target binding sequence of any amplification primer disclosed herein is also described.

Oligonucleotides described herein may be used to detect the presence of GV by selecting for an amplified nucleic acid sequence found in the genes that produce the toxins vaginolysin and cytolysin/hemolysin. In this regard, the inventors have elected to refer to this target as the vly gene. However, the literature also refers to the cytolysin gene and the hemolysin gene of GV. Whether or not these are different genes or simply different names for the same gene is immaterial to the invention described herein. While the target sequence is referred to herein as the "vly gene" or the "vly target" it is the target itself (i.e. a gene that produces one of the aforesaid toxins), and not the name of the gene target that is the focus of the present invention. Although applicants do not wish to be held to a particular theory, applicants believe that these toxins are all produced by the same gene. However, the present invention is not to be limited to the name of the GV gene in which the target sequence is located.

In one embodiment, there is disclosed herein a method for detecting a *Gardnerella vaginalis* target sequence. In this method at least one oligonucleotide primer is provided that will amplify at least some portion of the vly gene of GV and, after amplification, the amplified target sequence is detected. Examples of the vly gene of GV include SEQ ID NOs. 1, 2, 23, 24 and 25.

Highly conserved regions of the vly gene have been identified. The highly conserved sequence is at the location between about base pairs 328-523 on the vly gene (for strains 14018, 14019, and 49145 described herein). In a preferred embodiment, the target sequence is the highly conserved region of the vly gene.

The highly conserved target vly gene for strains 14018, 14019 and 49145 (that correspond to respective Genbank Acession Nos. EU522486, EU522487 and EU522488) are SEQ ID NOs. 1, 23, and 24. SEQ ID NOs. 2 and 25 are the highly conserved target vly gene for two clones (T10 and T11, respectively). The clones have Genbank Accession Numbers EU697811 and EU697812. The location of the highly conserved region in the clones is at about base pairs 331-526. The vly gene is highly conserved among the strains and clones, but there are variations among the strains and clones.

Within the vly gene there are advantageous target regions that themselves are highly conserved. One such target region is illustrated in FIG. 1 and is also identified as SEQ ID NO. 20. SEQ ID NO. 20 is base pairs 325-524 of SEQ ID NO. 1. Among the three strains of vly, there is no variation in SEQ ID NO. 20. However, FIG. 1 illustrates that there are minor sequence variations in this target region between the strains and clones of GV. Although the sequence is identical for all three strains, the sequence for each strain is illustrated (as 100, 110, and 120) in FIG. 1. SEQ ID NO. 21 is the sequence of the target region for the two clones (T10 and T11) and is identical for each of the two clones. However, there is some minor difference between SEQ ID NO. 20 and SEQ ID NO. 21. These variations of SEQ ID NO. 21 (with respect to SEQ ID NO. 20) are illustrated at 130 and 140 of FIG. 1. The variations are very minor: 7 base pairs from the 196 base pairs in the advantageous target sequence. Also, the variations are in the same locations for all of the sequences. The skilled person can design primers and probes that do not align to the locations on the target regions where variations are found.

As is noted from FIG. 1, the highly conserved target region of the vly gene is substantially identical for the various strains and clones identified above. Only the sense strand of the target region is illustrated in FIG. 1. Since the antisense strand is the complement of the sense strand, the antisense strand, although not specifically illustrated in FIG. 1, is known from the sequence listed in FIG. 1. The sequences in FIG. 1 are four nucleotides longer than SEQ ID NOs. 20 and 21, but are otherwise identical. The additional nucleotides are provided in FIG. 1 to more clearly illustrate the relationship between the primers and the target at the ends of the target sequence.

Oligonucleotide probe sets are described herein that are designed to select for this highly conserved region and offer a mechanism for detection. The probe set design is based upon a number of factors, chief among which is the assay in which the probe set is used. Assays for the detection of DNA or RNA sequences are well known in the art. These assays typically use some type of amplification or some type of imaging to confirm the presence of the target DNA. Examples of amplification reactions include PCR (polymerase chain reaction), SDA (strand displacement amplification), TMA (transcription mediated amplification) and LCR (ligase chain reaction).

of base pairs in the sequence as well as the type of bases in the sequence. These guidelines for designing oligonucleotides are well known to one skilled in the art and are not set forth in detail herein.

In one embodiment of the present invention, portions of the primers and probes for the SDA assay are complementary to the target region of the vly gene represented by SEQ ID NO. 20. The target is first denatured. The probe sets are configured such that the forward primers and probe bind to (i.e. are complementary to) the antisense strand of the denatured target and the reverse primers bind to the sense strand of the denatured target. The portions of the primers and probes that bind to the target for one embodiment of an SDA probe set are listed in the following Table 1 along with their location on the highly conserved portion of the vly gene. Since the highly conserved region of the vly gene is virtually identical for the various strains of GV, the highly conserved region of the vly gene for each strain or clone is not separately listed.

The oligonucleotide SDA primer/probe sets described herein are sufficiently complementary to these portions of the gene to selectively bind to these portions.

TABLE 1

Target Binding Sequences for SDA Primer and Probe Set

| SEQ ID Number | SEQUENCE | Description | Location* in the highly conserved region of vaginolysin (vly) |
|---|---|---|---|
| SEQ ID NO: 3 | AAT ATG CCA AGC CTG A | (region of amplification primer GV vly LP6 complementary to antisense strand of vly gene (or gvh gene) of GVH | 388-403 |
| SEQ ID NO: 4 | GCA AAT CAA CGC TCA A | (region of amplification primer GV vly RP7 complementary to sense strand of vly gene (or gvh gene) of GVH | 430-445 |
| SEQ ID NO: 5 | GCA AAC CGC GCT CCA A | (region of reporter probe GV vly DT5 complementary to antisense strand of vly gene (or gvh gene) of GVH | 409-424 |
| SEQ ID NO: 6 | GTA TAC CCA GGT GCT | (left or forward bumper primer GV vly LB7 complementary to antisense strand of vly gene (or gvh gene) of GVH | 343-357 |
| SEQ ID NO: 7 | GCG CTG AAC AGT TAC | (right or reverse bumper primer GV vly RB8 complementary to sense strand of vly gene (or gvh gene) of GVH | 472-486 |

*GenBank Accession Number EU522486

In one embodiment, the amplification mechanism selected for detection is SDA. SDA is an isothermal amplification mechanism and therefore does not involve thermal cycling. As such SDA probe sets are designed for a target melting temperature ($T_m$) within a predetermined narrow range. Target melting temperature ($T_m$) is the temperature at which at least fifty percent of the oligonucleotide is annealed to its perfect complement. One skilled in the art is aware that the $T_m$ of an oligonucleotide sequence is determined by the number For the SDA embodiment described herein, the oligonucleotide probe set has left and right bumper primers, left and right amplification primers and a probe. As indicated above, the left or forward primers and probes bind to the antisense strand of the vly gene and the reverse or right primers bind to the sense strands. Thus, the portions of the vly gene to which these primers and probes bind are sufficiently complementary to the target binding sequences SEQ ID NOS. 3-7 to facilitate hybridization of the primers and probes thereto.

The primers and probe may have additional nucleotides or sequences attached thereto. The probe also has additional imaging moieties affixed thereto. These moieties facilitate the detection of the target DNA sequence. Using such an oligonucleotide probe set, an SDA assay may be performed on a sample in order to determine the presence or absence of most strains of GV. In one illustrative embodiment, about a 144 base pair region of the vly gene is amplified between a section of the vly gene at about base pair 343 to about base pair 486 of the vly gene.

Other embodiments of the invention use different oligonucleotide sequences that bind to the above-described vly gene region. Primer/probe sets are configured to not only selectively bind in this region of the vly gene, but to amplify some portion of the vly gene sequence for detection. The oligonucleotides described herein have a sequence that is sufficiently complementary to either the sense or the antisense strand of the denatured target nucleic acid sequence to render it capable of binding to the target. The oligonucleotides described herein may also be used, either alone or in combination, to facilitate detection through amplification of the vly gene nucleic acid sequence. In one embodiment, the probes are designed to perform a Taqman® real-time PCR assay on the target portion of the gene. Examples of two probe sets used for Taqman® real-time PCR assays, described in terms of their oligonucleotide sequences, are:

assay are used in combination as amplification primers, bumper primers and a detector in that assay.

In another embodiment, a kit is provided for the detection of GV. The kit includes one or more of the oligonucleotides described herein that selectively bind to the vly gene of GV and are capable of amplifying a target sequence that may be used for detection of that organism. The kit is provided with one or more of the oligonucleotides and buffer reagents for performing amplification assays.

In one aspect of the kit, oligonucleotides and reagents for purposes of SDA may be provided. In this aspect, two oligonucleotides are provided as amplification primers, two oligonucleotides are provided as bumper primers and one oligonucleotide may be provided for use as a detector.

In yet another aspect of the kit, the oligonucleotides for SDA purposes may be provided in dried or liquid format. In dried format, the composition may be applied to an appropriate receptacle where sample and proper SDA buffers may be added to perform the assay.

In yet another aspect of the kit, oligonucleotides and reagents for purposes of Taqman PCR may be provided. In this aspect, three oligonucleotides are provided. Two of the three are amplification primers and the third oligonucleotide is configured as a detector.

In exemplary embodiments, the kit for an amplification or detection reaction has an oligonucleotide having a target

TABLE 2

Primer/Probe Sets for Quantitative Real Time PCR

| SEQ ID NO. | Description | Oligonucleotides 5' Sequence 3' | ORF Location (bp)* |
|---|---|---|---|
| SEQ ID NO: 8 | GVvlyForward 1 | GGC GGC GAA AGT GCT GTA | 457-474 |
| SEQ ID NO: 9 | GVvlyReverse 1 | AGC CGT TCA CTG CGG AAG T | 505-523 |
| SEQ ID NO: 10 | GVvlyProbe 1 | (6FAM)-TTC AGC GCC CAA CCA AGA GCT CTG T-(TAMRA) | 479-503 |
| SEQ ID NO: 11 | GVvlyForward 2 | GCC AAC GAT GAT CGC GTA T | 328-346 |
| SEQ ID NO: 12 | GVvlyReverse 2 | CAG GCT TGG CAT ATT GTC CAT | 382-402 |
| SEQ ID NO: 13 | GVvlyProbe 2 | (6FAM)-CCC AGG TGC TCT TTT CCG TGC TGA-(TAMRA) | 348-371 |

*Accession No. EU522486

In the PCR assays, the forward primers and probes are sufficiently complementary to hybridize to the antisense strand of the target nucleic acid (under appropriate conditions) and the reverse primers are sufficiently complementary to hybridize to the sense strand of the target nucleic acid (under appropriate conditions). FIG. 2 illustrates the binding location of the primers and probes described in Table 2 relative to the sense strand of the target sequence (the boxed portion of the sequence indicates the location of the specific primer/probe associated with the box.

In yet another embodiment, the oligonucleotides may be used in a method for detecting the presence or absence of GV in a sample. In a further embodiment, the method includes treating a sample using one or more oligonucleotides specific for the target sequence in a nucleic acid amplification reaction and detecting the presence or absence of the amplified nucleic acid product.

In one illustrative embodiment, SDA is selected as the amplification reaction. In the context of this embodiment, the oligonucleotides described herein as suited for use in the SDA binding sequence that is any one of SEQ ID NOs: 3 to 13 and complements thereof, and sequences that share at least 70% sequence similarity with SEQ ID NO. 3 to 13 and complements thereof. In other embodiments, the kit has an oligonucleotide having a target binding sequence that is any one of SEQ ID NOs: 3 to 13 and complements thereof, and sequences that share at least 80% sequence similarity with SEQ ID NO. 3 to 13 and complements thereof. In other embodiments, the kit has an oligonucleotide having a target binding sequence that is any one of SEQ ID NOs: 3 to 13 and complements thereof, and sequences that share at least 90% sequence similarity with SEQ ID NOs. 3 to 13 and complements thereof. In other embodiments, the kit has an oligonucleotide having a target binding sequence that is any one of SEQ ID NOs: 3 to 13 and complements thereof.

The present invention also provides a method for detecting a *Gardnerella vaginalis* target sequence comprising: (a) hybridizing one or more amplification primers disclosed herein to a target sequence in the target vly gene for GV and (b) detecting said hybridized amplification primer. In the method at least one amplification primer is a reporter probe that further comprises a detectable label. Examples of detectable labels include TAMRA, 6ROX, or 6FAM.

BRIEF DESCRIPTION OF THE FIGURES

FIG. 3 illustrates both the sense and antisense strands of nt 328-523 of the target region and the relative hybridization positions of an exemplary SDA primer/probe probe set in the target region and with the hybridization positions of the primers and probe further illustrated by outlining on the sense strand of the target region; and FIG. 4 illustrates both the sense and antisense strands of an IAC for the method described herein and the relative hybridization positions of an exemplary SDA primer/probe probe set in the target region and with the hybridization positions of the primers and probe.

DETAILED DESCRIPTION OF THE INVENTION

Figure 1:
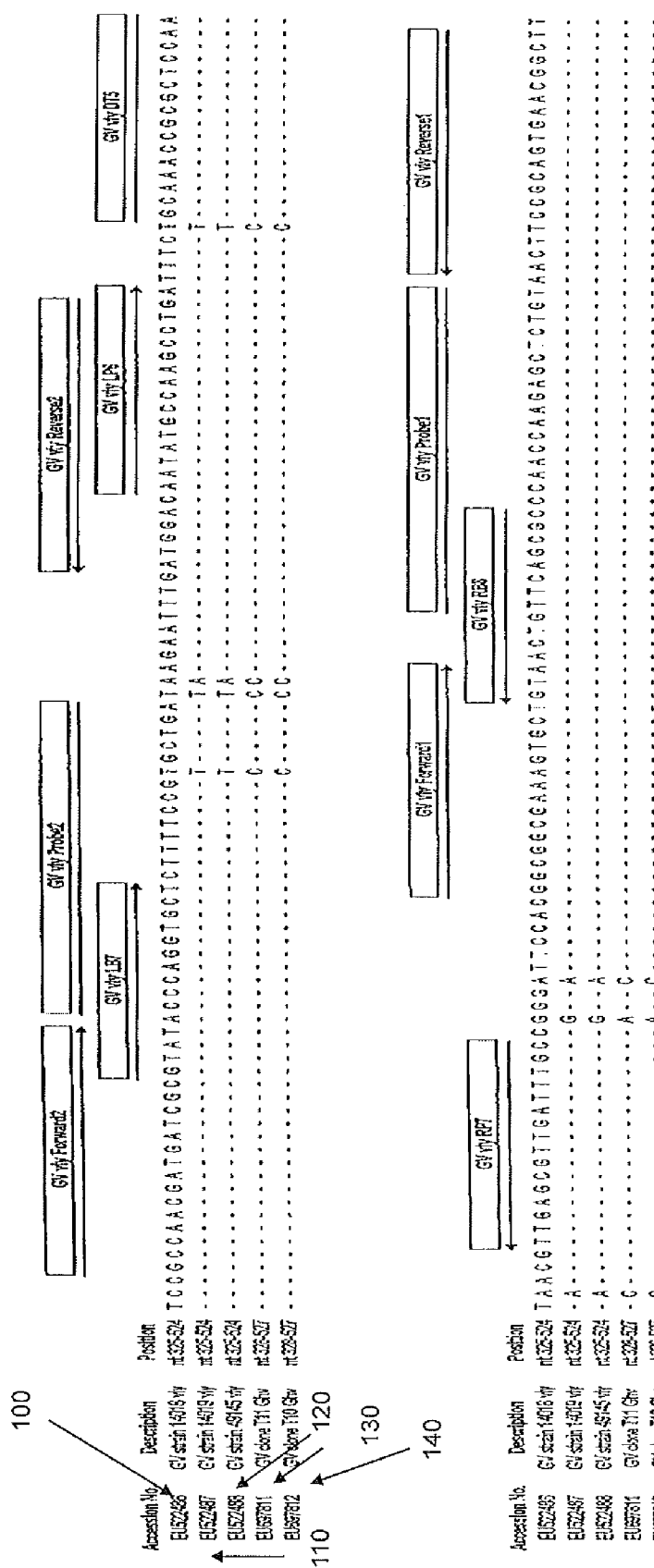
FIG. 1 illustrates the sense strand of the target region of the vly gene of GV and variations in the sense strand sequence for various GV strains and clones and the hybridization positions of embodiments of primers and probes described herein relative to the sense strand.
Figure 2:
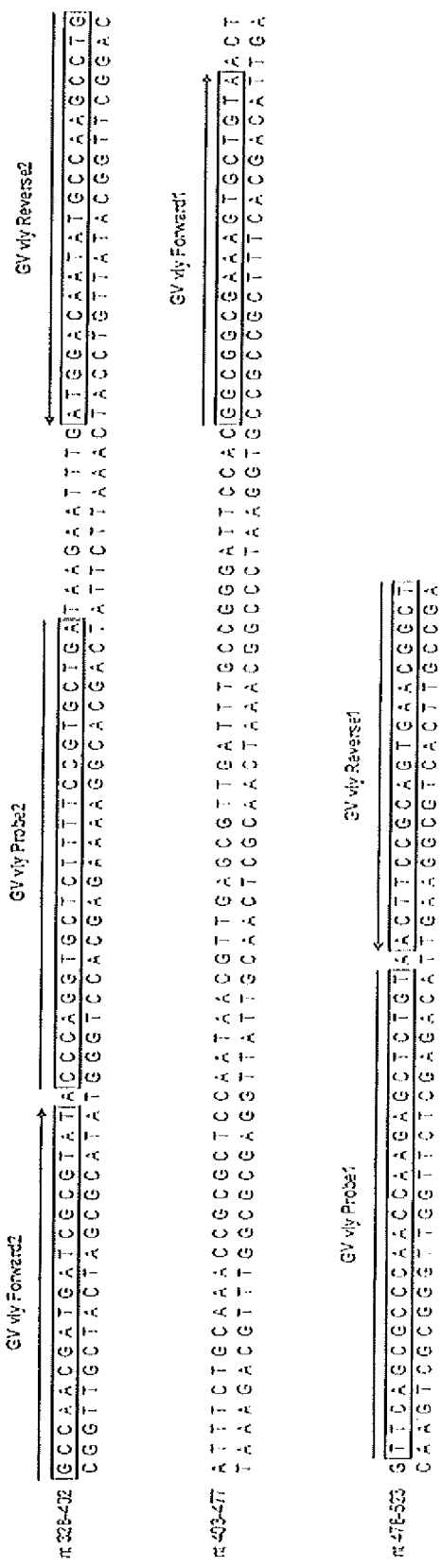
FIG. 2 illustrates both the sense and antisense strands of nt 328-523 of the target region and the relative hybridization positions of two exemplary PCR probe sets in the target region and with the hybridization positions of the primers and probes further illustrated by outlining on the sense strand.

Any definitions provided are for reason of clarity and should not be considered as limiting. Except where noted, the technical and scientific terms used herein are intended to have the same meaning as commonly understood by one of ordinary skill in the art to which the invention pertains.

Described herein are nucleic acid amplification methods and assays for the detection and/or quantitation of nucleic acid sequences of *Gardnerella vaginalis* (GV). The present invention provides one or more oligonucleotides that are complementary or that anneal to nucleic acid sequences of *Gardnerella vaginalis* for the amplification and/or detection of said sequences. In one embodiment of the present invention, an internal amplification control (IAC) is provided. The IAC can be used in nucleic acid amplification assays of the invention to determine whether the assay conditions are permissible for amplification and/or detection of a target sequence. The oligonucleotides may be used in all types of amplification reactions such as, for example, Strand Displacement Amplification (SDA), Polymerase Chain Reaction (PCR), Ligase Chain Reaction, Nucleic Acid Sequence Based Amplification (NASBA), Rolling Circle Amplification (RCA), Transcription Mediated Amplification (TMA) and QB Replicase-mediated amplification.

The methods of the invention are particularly advantageous over traditional methods used for the detection of *Gardnerella vaginalis*, as they detect the organism itself, rather than prior art detection methods and kits, that detect the toxins (e.g. vaginolysin) that are produced by the organism rather than the organism itself.

Sensitivity of an assay relates to the tolerance of false negatives. A test result is false negative if the test result is negative but the sample actually contains the target sequence. The smaller the amount of target sequence an assay can detect, the higher sensitivity an assay has.

Specificity of an assay relates to the tolerance of false positives. A test result is false positive if the test result is positive but the sample actually does not contain the target sequence. Thus, the more specific an assay, the lower the level of false positive results.

In accordance with an embodiment of the present invention, a result of an assay to detect for *Gardnerella vaginalis* in a sample that utilizes an IAC can be interpreted as described in Table 3.

TABLE 3

Interpretation of a Diplex SDA Assay

| | Result | | | |
|---|---|---|---|---|
| IAC | + | − | + | − |
| Target Sequence for *Gardnerella vaginalis* | − | + | + | − |
| Presence or absence of *Gardnerella vaginalis* | Absence | Presence | Presence | Inhibitory reaction, assay needs to be re-performed or modified |

An IAC may be used instead of, and/or in addition to, a conventional amplification control (AC). It is understood by one skilled in the art that the conventional AC reaction is performed in a separate reaction mixture from the sample to be tested. A conventional AC reaction comprises amplification reagents and target DNA. If the amplification and/or detection of the target DNA in the AC reaction is suppressed, an indication that the target sequence is absent from a test sample may be attributed to inhibitory signals in the reaction. While this form of control reaction is effective, it is not the most desirable. Since the AC reaction is performed separately, it cannot exactly reflect the conditions of the reactions containing the test sample. The methods of the invention are particularly useful in that they have an IAC and the control reaction is performed under identical spatial and temporal conditions as the amplification and/or detection of the target sequence thereby minimizing human error.

Described herein are amplification primers that anneal to a target sequence (i.e., a sequence of *Gardnerella vaginalis*). In those embodiments where an IAC is used, amplification primers are provided that anneal to the IAC. In some embodiments of the invention a bumper primer or its respective target binding sequence described in Table 1 or FIGS. 1, 3 and 4 may be used as an amplification primer. In some embodiments of the invention, an amplification primer is chosen from the amplification primers described in Tables 1 and 2 or FIGS. 1-4 as disclosed herein. In another embodiment of the invention, an amplification primer is chosen from the target binding sequences of amplification primers described in FIGS. 1-4 as disclosed herein.

Amplification Methods

The oligonucleotides disclosed herein can be used in any method of nucleic acid amplification known in the art.

Suitable amplification methods include, but are not limited to, Polymerase Chain Reaction ("PCR"; see U.S. Pat. Nos. 4,683,195; 4,683,202; 4,800,159; and 4,965,188), Strand Displacement Amplification ("SDA"; see Walker et al., *Proc. Nat'l Acad. Sci. USA* 89:392 (1992); Walker et al., *Nucl. Acids Res.* 20:1691 (1992); and U.S. Pat. No. 5,270,184, the disclosure of which is hereby incorporated in its entirety by reference), thermophilic Strand Displacement Amplification ("tSDA"; see EP 0 684 315), Self-Sustained Sequence Replication ("3SR"; see Guatelli et al., *Proc. Nat'l Acad. Sci. USA* 87:1874-78 (1990)), Nucleic Acid Sequence-Based Amplification ("NASBA"; see U.S. Pat. No. 5,130,238), Qβ replicase system (see Lizardi et al., BioTechnology 6:1197 (1988)); Ligase Chain Reaction ("LCR"; see U.S. Pat. No. 5,427,930); Rolling Circle Amplification (see Lizardi et al., *Nat Genet* 19:225-232 (1998)) and transcription based amplification (see Kwoh et al., *Proc. Nat'l Acad. Sci. USA* 86:1173-77 (1989)). The amplification primers of the present invention may be used to carry out PCR, SDA or tSDA.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: SDA; 3SR; the Qβ replicase system; and the techniques disclosed in WO 90/10064 and WO 91/03573. Examples of techniques that require temperature cycling are: PCR; LCR; transcription-based amplification; and restriction amplification (U.S. Pat. No. 5,102,784).

SDA generally proceeds along the following pathway. First, amplification primers bind to a target sequence or to a displaced single-stranded extension product that has been previously polymerized. Second, a 5'-3' exonuclease-deficient polymerase incorporates an α-thiodeoxynucleoside triphosphate ("α-thio dNTP") into an extension product. If the α-thio dNTP is α-thio dCTP, for example, it is incorporated into the extension product wherever there is a complementary G residue in the template. Incorporation of an α-thio dNTP into the extension product at a restriction endonuclease recognition site creates a hemimodified site, i.e. a site modified only on the extension product strand. A restriction endonuclease then nicks the hemimodified double-stranded restriction site. Next, the restriction endonuclease dissociates from the nick site. Finally, a polymerase that is deficient in 5'-3' exonuclease activity extends from the 3' end of the nick and displaces the downstream strand of DNA. Nicking, strand extension and strand displacement occur concurrently and continuously because extension from the nick regenerates another nickable restriction site. When a pair of amplification primers is used that each hybridize to one of the two strands of a double-stranded duplex comprising a target sequence, amplification is exponential because both the sense and antisense strands serve as templates in each round of amplification. When a single amplification primer is used, amplification is linear because only one strand serves as a template for primer extension. Examples of restriction endonucleases that nick their double-stranded recognition sites when an α-thio dNTP is incorporated and that are suitable for SDA include BsoB1, BsrI, BstNI, BsmAI, BstOI, BslI, AvaI, HincII and NciI. SDA is further described in U.S. Pat. Nos. 5,270,184, 5,455,166 and 5,648,211, which are incorporated by reference herein in their entirety. A SDA assay can be, but is not limited to, a traditional (or conventional) SDA (as described in Walker et al., PNAS (1992) 89:392-396, U.S. Pat. Nos. 5,962,273, 5,712,124, and 5,744,311, each of which is incorporated herein by reference), a thermophilic SDA (+SDA as described in Walker et al., Nuc. Acids Res. (1992) 20:1691-1696, U.S. Pat. Nos. 5,648,211 and 5,744,311, each of which is incorporated herein by reference), and a homogeneous real-time fluorescent thermophilic SDA (as described in U.S. Pat. No. 6,379,888, which is incorporated herein by reference).

Cross-contamination with amplification products carried over from previous amplification reactions in reagents, pipetting devices and laboratory surfaces may be reduced by incorporating various residues into extension products. For example, thymine may be substituted with 2'-deoxyuridine 5' triphosphate ("dU"), as is taught in EP 0 624 643. Excision of dU that is incorporated into amplification products is catalyzed by uracil DNA glycosylase ("UDG"), which renders amplification products containing dU incapable of further amplification. The UDG itself may be inactivated when appropriate to continue amplification.

In the case of tSDA, primers and their target sequences preferably are selected such that their GC content is less than 70% of the total nucleotide composition to minimize secondary structure and primer-primer interactions that may limit target amplification efficiency. A suitable amplification primer for tSDA comprises, in order from the 3' end of the probe to the 5' end, a target binding sequence, a restriction endonuclease recognition site, and a "tail." The target binding sequence hybridizes specifically to a complementary sequence of the target nucleic acid. The restriction endonuclease recognition site is recognized by a restriction endonuclease that nicks one strand of a DNA duplex when the recognition site is hemimodified, as described by Walker et al., *Proc. Nat'l Acad. Sci. USA* 89:392 (1992) and Walker et al., *Nucl. Acids. Res.* 20:1691 (1992). The 5' tail functions as a polymerase repriming site when the remainder of the amplification primer is nicked and displaced during tSDA. The repriming function of the tail sustains the tSDA reaction and allows synthesis of multiple amplicons from a single target molecule. The length and sequence of the tail region may vary, provided that the tail remains hybridized to the target after nicking and that the tail does not contain sequences that will hybridize either to the target binding sequence or to other primers.

Some amplification methods, such as tSDA, use a "bumper primer" or "external primer" to displace primer extension products. A "bumper primer" or "external primer" is a primer used to displace an amplification primer and its extension product in an amplification reaction. A bumper primer anneals to a target sequence upstream of an amplification primer such that extension of the bumper primer displaces the downstream amplification primer and its extension product. Primer extension products alternatively may be displaced by heating. Bumper primers may hybridize to any target sequence that is upstream from the amplification primers and that is sufficiently close to the binding site of the amplification primer to displace the amplification primer extension product upon extension of the bumper primer. Mismatches between the bumper primer sequence and target sequence generally do not affect amplification efficiency, provided the bumper primer still hybridizes to the target sequence. Furthermore, the specificity of the SDA system for amplification of the target sequence in preference to other nucleic acids is not dependent upon the specificity of the bumper primer(s) for hybridization to the target nucleic acid. The specificity of an SDA system for the target sequence is derived from the fidelity of hybridization of the SDA primers and probes or oligonucleotides used for detection of amplified products.

When an amplification reaction used in accordance with the invention is a tSDA reaction, the polymerases that can be used include, but are not limited to, exo⁻ Vent (New England Biolabs), exo⁻ Deep Vent (New England Biolabs), Bst (Bio-Rad), exo⁻ Pfu (Stratagene), Bca (Panvera), and Sequencing Grade Taq (Promega). Others may be routinely identified using the foregoing extension assay. The polymerases Tth (Boehringer), Tfi (Epicentre), REPLINASE (DuPont) and REPLITHERM (Epicentre) are able to displace a strand from a nick, but they also have 5'-3' exonuclease activity. These polymerases are useful in the methods of the invention after removal of the exonuclease activity, e.g., by genetic engineering. As the thermostability of thermophilic restriction endonucleases is generally limited to less than 65° C., thermophilic polymerases with optimal activity around this temperature or lower (e.g., Bst and Bca) are more compatible with thermophilic restriction endonucleases in the reaction.

The components of the present invention may be optimized to a form where each component could be dried and rehydrated when needed by using any technique known in the art. (See Little et al., Clinical Chemistry 45(6):777-784 (1999), which is incorporated herein by reference).

Primer Design

An "amplification primer" is an oligonucleotide for amplification of a target sequence by extension of the oligonucleotide after hybridization to a target sequence or by ligation of multiple oligonucleotides that are adjacent when hybridized to the target sequence. At least a portion of the amplification primer hybridizes to the target sequence. This portion is referred to as the target binding sequence and it determines target-specificity of the primer. It should be understood that the target binding sequences exemplified in the present invention may also be used in a variety of other ways for detection of GV. For example, the target binding sequences disclosed herein may alternatively be used as hybridization probes for direct detection of GV, either without prior amplification or in a post amplification assay. Such hybridization methods are well known in the art and typically employ a detectable label associated with or linked to the target binding sequence to facilitate detection of hybridization.

The design of amplification primers may be optimized for each method of amplification. As no special sequences or structures are required to drive the amplification reaction, amplification primers for a Polymerase Chain Reaction (PCR) may consist only of template binding sequences. However, other amplification reactions require specialized nucleotide sequences, in addition to the target binding sequence, in order for the reaction to proceed. For example, an amplification primer for use in a SDA assay further comprises a restriction endonuclease recognition site 5' to the target binding sequence (see U.S. Pat. Nos. 5,455,166 and 5,270,184). The amplification primer may also comprise a 3'—OH group, which is extendable by DNA polymerase when the template-binding sequence of the amplification primer is annealed to the target sequence. Amplification primers for Self-sustained Sequence Replication (3SR) and Nucleic Acid Sequence-Based Assay (NASBA), in contrast, comprise an RNA polymerase promoter near the 5' end. (3SR assays are described in Guatelli et al., 1990, Proc. Natl. Acad. Sci. USA 87:1874-1878) The promoter is appended to the target binding sequence and serves to drive the amplification reaction by directing transcription of multiple RNA copies of the template. Such sequences in addition to the target binding sequence that are necessary for a particular amplification reaction are well known in the art.

In designing the amplification primers and the bumper primers of the present invention, general concerns known in the art should be taken into account. For example, when a target sequence comprising a large number of GC and AT repeats is used for designing a primer, care should be taken to minimize potential dimer interactions to avoid self-hybridization of primers. Primers that can form four or more consecutive bonds with itself, or eight or more inter-strand bonds with other primers should be generally avoided. Primers that can form 3' dimers should especially be avoided, because hybridizing at the 3' ends of the primer, even transiently, will lead to extension of the primer due to polymerase action and ruining of the primer. Certain computer software programs (e.g., Oligo™, National Biosciences, Inc., Plymouth, Minn.) can be used in designing of the primers to avoid the problems. Primer combinations are also screened for optimal conditions.

As is known in the art, annealing or hybridization of complementary and partially complementary nucleic acid sequences may also be obtained by adjustment of the reaction conditions to increase or decrease stringency (e.g., adjustment of temperature or salt content of the buffer). Such modifications of the disclosed sequences and any necessary adjustments of conditions are encompassed by the present invention. Information relating to buffer conditions can be found in Experimental Design in Biotechnology by Dr. Perry Haaland (Marcell Dekker, NY, 1989), incorporated herein by reference in its entirety.

In the embodiments that deploy an IAC, a diplex amplification reaction, an amplification primer is designed to be able to hybridize to both a GV target sequence and an IAC sequence and amplify the sequence to which it is hybridized. This is achieved by using a shared nucleic acid sequence between GV target sequence and an IAC sequence to design an amplification primer. Other sequences, as required for performance of a selected amplification reaction, may optionally be added to an amplification primer as disclosed herein.

By way of example, but not limitation, amplification primers for use in a SDA assay generally comprise a 3' template-binding sequence, a nickable restriction endonuclease recognition site 5' to the template-binding sequence, and a tail sequence about 10-25 nucleotides in length 5' to the restriction endonuclease recognition site. Such amplification primer may contain a recognition site for the restriction endonuclease BsoBI, which is nicked during the SDA reaction. It will be apparent to one skilled in the art that other nickable restriction endonuclease recognition sites may be substituted for the BsoBI recognition site. The tail sequence should not contain the restriction site used for SDA and sequences which will anneal either to its own target binding sequence or to the other primers (e.g., bumper primers).

In some embodiments, a pair of amplification primers is used, each of which anneals to one of the two strands of a double stranded target sequence or IAC sequence. In this case, amplification is exponential because both the sense and antisense strands serve as templates for the opposite primer in subsequent rounds of amplification. When a single amplification primer is used, amplification is linear because only one strand serves as a template for primer extension.

In some embodiments, the methods of the present invention encompass an amplification primer that comprises a nucleotide sequence consisting essentially of SEQ ID NO: 3 and 4 or their respective target binding sequences. In other embodiments, the methods of the present invention encompass at least two amplification primers, wherein a first amplification primer comprises a nucleotide sequence consisting essentially of SEQ ID NO: 3 or its respective target binding sequences; and a second amplification primer comprises a nucleotide sequence consisting essentially of SEQ ID NO: 4 or its respective target binding sequences.

In some embodiments, the methods of the present invention encompasses one or more bumper primers. A bumper primer is a primer used to displace an amplification primer and its extension product in an amplification reaction. A bumper primer anneals to a target sequence upstream of an amplification primer, such that extension of the bumper primer displaces the downstream amplification primer and its extension product. A bumper primer may also function as an amplification primer. In some embodiments, the methods of the present invention encompass one or more bumper primers. In certain embodiments, the bumper primer comprises an oligonucleotide having the sequence comprising SEQ ID NO: 6 or 7. In one embodiment, a bumper primer comprises an oligonucleotide having a partial or complete sequence of SEQ ID NO: 6 or 7. In another embodiment, the methods of the present invention encompass at least two bumper primers, wherein a first primer comprises a nucleotide sequence consisting essentially of SEQ ID NO: 6 and a second primer comprises a nucleotide sequence consisting essentially of SEQ ID NO: 7.

The primer/probes described herein are described in terms of being 100% complementary to their target binding sequences. However, based on the primer design conditions described above, primers and probes can bind to target sequences even though they are less than 100% complementary with those regions. The requisite degree of complementarity depends on a variety of factors including the stringency of the binding conditions. Depending upon the stringency conditions employed, the primers and probes may be modified to include different bases in their sequence and still be sufficiently complementary to bind to the target region. Sufficiently complementary, as used herein includes complementarity of 70% or more. In preferred embodiments, the complementarity of the primers/probes to their target sequence is at least 80% over the length of the binding portion of the primers/probes. More preferably, the complementarity of the primers and probes to their target sequences is 90% or more.

Target Sequences

"Target" or "target sequence" refers to a GV nucleic acid sequence to be amplified and/or detected. A target or target sequence includes the GV nucleic acid sequence to be amplified and any complementary second strand. In some embodiments, a target sequence may be single-stranded or double-stranded, in which case, either one or both strands can bind to an amplification primer. A target or target sequence may also comprise a nucleotide sequence that is recognized by an adapter oligonucleotide (i.e., adapter-binding sequence). The primers of the present invention are designed to anneal to a region of the vly gene of GV as identified in SEQ ID NOs. 1, 2, and 23-25. The target sequence is preferably the target regions identified in SEQ ID NOS. 20 and 21.

Internal Amplification Control

"Internal amplification control", "IAC" or "IAC sequence" refers to a nucleic acid sequence comprising a sequence that anneals to an amplification primer and a sequence that can be detected separately from the target sequence. Any detection method known in the art may be employed.

In accordance with the present invention, an IAC sequence is designed to share nucleic acid sequences with a GV target sequence, thus the same amplification primer(s) can amplify both an IAC sequence and a target sequence if it is present in a sample. An IAC sequence is also designed to have some nucleic acid sequences that differ from a GV target sequence, so that the detection of the IAC sequence and the target sequence may be differentiated. Since an IAC sequence is amplified and/or detected in the same reaction mixture as a target sequence, diplex assays have the advantage of detecting human error or an inhibitory reaction condition, e.g., the presence of an inhibitor or absence of a critical reagent. The presence of an IAC in the same reaction as the sample to be tested eliminates the need for separate amplification control reactions as required by the current monoplex SDA assays.

Although not intending to be bound by a particular mechanism of action, the presence of an IAC in the same reaction as a target sequence allows the amplification assay of the present invention to detect the presence of inhibitors of the reaction and/or conditions that may indicate a false negative result. As used herein, a false negative result refers to a result that indicates no detection of a target sequence, however, such indication is not due to the absence of the target sequence in the sample, but due to human error or a reaction condition, e.g., the lack of a critical reaction element, or the existence of an inhibitor of the reaction, or a mistake in performing the assay.

A detection method is used wherein such method differentiates amplification products of a target sequence from amplification products of an IAC sequence. In one embodiment, the amplification products of the target sequence and the IAC may be detected by different dye labeled detection probes. In one example, fluorescein is used to detect amplification products of the target sequence and rhodamine fluorescence is used to detect the amplification products of the IAC.

In some embodiments, an IAC sequence is designed such that either its 3' or 5' terminus contains a sequence in common with a GV DNA sequence. In some other embodiments, an IAC is designed such that both the 3' and 5' terminus contain sequences in common with a DNA sequence for an amplification primer to bind.

An IAC sequence is also designed to comprise a nucleic acid sequence that is different from the GV target sequence to be amplified, such that the detection of the amplification products of the IAC and the target sequence can be differentiated.

In some embodiments, the methods of the present invention utilize an IAC that comprises a nucleotide sequence consisting essentially of SEQ ID NO:19. Note that SEQ ID NO: 19 is quite similar to SEQ ID NOs. 20 and 21 (the preferred target binding sequences) except for the region where the detector (GVvlyACD2b) binds to the IAC target. GVvlyACD2b is identified herein as SEQ ID NO. 22. Other than the detector, the bumpers and primers for the IAC target are the same bumpers and primers for SDA (SEQ ID NOs. 14-17).

The primers described above are described in terms of being 100% complementary to their target binding sequences. As described below, primers and probes can bind to target sequences even though they are less than 100% complementary with those regions. The requisite degree of complementarity depends on a variety of factors including the stringency of the binding conditions. Depending upon the stringency conditions employed, the primers and probes may be modified to include different bases in their sequence and still be sufficiently complementary to bind to the target vly gene. Sufficiently complementary, as used herein include complementarity of 70% or more. In preferred embodiments, the complementarity of the primers/probes to their target sequence is at least 80% over the length of the binding portion of the primers/probes. More preferably, the complementarity of the primers and probes to their target sequences is 90% or more.

While the oligonucleotides described herein must be sufficiently complementary to bind their respective portions of the target, it is recognized at some point the sequence of the oligonucleotide becomes less complementary to the target sequence and may bind other nucleic acid sequences. Therefore, it is desirable that the oligonucleotide probes remain sufficiently complementary with its respective portion of the target, and not lose selectivity for its respective target binding site.

Detection of Nucleic Acids

The amplification products generated using one or more primers of the invention can be detected by any method known in the art. As used herein, amplification products include both the amplified target sequences and the amplified IAC sequences. Amplification products can be detected by hybridization to a labeled probe using conventional techniques, for example, one that hybridizes to amplified nucleic acids at a sequence that lies between the amplification primers. Alternatively, amplification products may be detected by their characteristic size, for example by electrophoresis followed by ethidium bromide staining to visualize the nucleic acids. In a further alternative, a labeled amplification primer is used. In a still further alternative, a labeled amplification primer/internal probe is extended on the target sequence, as described by Walker et al., *Proc. Nat'l Acad. Sci. USA* 89:392 (1992); or Walker et al., *Nucl. Acids Res.* 20:1691 (1992). In another embodiment, detection is accomplished directly through hybridization and extension of a labeled reporter probe as described in U.S. Pat. Nos. 5,928,869 and 5,958,700. Detection methods also include a chemiluminescent method in which amplified products are detected using a biotinylated capture probe and an enzyme-conjugated detector probe, as described in U.S. Pat. No. 5,470,723. After hybridization of these two probes at different sites between the two amplification primer binding sites, the complex is captured on a streptavidin-coated microtiter plate, and the chemiluminescent signal is developed and read in a luminometer.

In an embodiment of the present invention, the detection method should detect both the target amplification products and the IAC amplification products (if present), and differentiate between the amplification products detected. Any method known in the art capable of achieving this purpose can be used. For example, the detection methods that are disclosed in Walker et al., Nucl. Acids Res., (1992) 20:1691-1696, the U.S. Pat. Nos. 5,648,211, 5,962,273, 5,814,490, 5,928,869, 6,316,200, and European Patent EP 0 678 582 (each of which is incorporated herein by reference) can be used in accordance with the present invention. In another embodiment, universal probes and methods for detection of nucleic acids are used (see U.S. Pat. No. 6,379,888, which is incorporated herein by reference).

Many donor/quencher dye pairs known in the art are useful in the present invention. These include, but not limited to, for example, fluorescein isothiocyanate (FITC)/tetramethylrhodamine isothiocyanate (TRITC), FITC/Texas Red. (Molecular Probes), FITC/Rhodamine X, FITC/tetramethylrhodamine (TAMRA), 6-Carboxyfluorescein (6-FAM)/TAMRA and others. The selection of a particular donor/quencher pair is not critical. For energy transfer quenching mechanisms it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl)aminonaphthalene (EDANS). Any dye pair which produces fluorescence quenching in the detection probe of the invention can be used in the methods of the invention, regardless of the mechanism by which quenching occurs. Terminal and internal-labeling methods are also known in the art and may be routinely used to link the donor and quencher dyes at their respective sites in the detection probe.

The present invention provides detection probes that are single-stranded oligonucleotides comprising SEQ ID NO: 5, 10 or 13 and a label. In certain embodiments, the label comprises at least one fluorescent donor/quencher pair linked to the oligonucleotide, wherein the fluorescent moiety is TAMRA or 6-FAM. For the IAC the fluorescent moiety is ROX.

In some embodiments, the present invention provides diplex homogeneous real-time fluorescent thermophilic SDA (tSDA). Homogeneous real-time fluorescent thermophilic SDA is a modified tSDA which detects nucleic acid target sequences by fluorescence quenching mechanisms (see, e.g., U.S. Pat. No. 6,379,888, which is incorporated herein by reference in its entirety). For example, in one embodiment, a detection probe may comprise a fluorescent donor/acceptor pair so that fluorescent quenching occurs in the absence of a target sequence. Although not intending to be bound by a particular mechanism of action, in the absence of hybridization of the detection probe to a second oligonucleotide (which is produced by amplification of a target sequence), the probe adopts a conformation which brings the donor and quencher into close spatial proximity and results in quenching of donor fluorescence. The probe may fold into an ordered secondary structure (e.g., a G-quartet, hairpin or triple helix), into a random coil, or into any other conformation which brings the donor and quencher into close enough proximity to produce fluorescence quenching. However, when the detection probe hybridizes to a second oligonucleotide, the intramolecularly base-paired secondary structure of the detection probe becomes unfolded or linearized, which increases the distance between the donor and the quencher and thereby reducing or eliminating fluorescence quenching. Alternatively, the detection probe may be designed as a linear detection probe (i.e., it does not fold into a secondary structure), wherein the distance between the donor and the quencher is short enough to produce fluorescence quenching. In this case (and optionally in cases where a non-linear detection probe described herein is used), the detection probe also contains a restriction endonuclease recognition site (RERS) between the fluorescent donor/quencher pair. The intermolecular base-pairing between the detection probe and a second oligonucleotide renders the RERS double-stranded and thereby cleavable or nickable by a restriction endonuclease. Although not intending to be bound by a particular mechanism of action, cleavage or nicking by the restriction endonuclease separates the donor and acceptor onto separate nucleic acid fragments, which leads to decreased quenching.

An associated change in a fluorescence parameter (e.g., an increase in donor fluorescence intensity, a decrease in acceptor fluorescence intensity or a ratio of the donor and/or acceptor fluorescence intensities) may be monitored in accordance with the methods of the invention to detect and/or monitor the presence of the target sequence. Monitoring a change in donor fluorescence intensity is usually preferred, as this change is typically larger than the change in acceptor fluorescence intensity. Other fluorescence parameters such as a change in fluorescence lifetime may also be monitored in accordance with the invention.

Kits

The present invention also provides kits for amplification and/or detection of GV nucleic acids comprising one or more amplification primers consisting essentially of SEQ ID NOS: 8-18 or their respective target binding sequences and at least one container which contains such primers. The kit may optionally include any one or more of: an IAC, adapter oligonucleotides, or detection probes. The kit may further include other components and reagents for performing a hybridization or amplification reaction, such as Southern hybridization, dot blot hybridization, PCR, or SDA. For detection by hybridization, a appropriate solution to perform hybridization may be included, e.g., 0.3 M NaCl, 0.03 M sodium citrate, 0.1% SDS. Components for detection methods also may be included in the kit, e.g., a second probe, a radiolabel, an enzyme substrate, an antibody and the like. Reagents appropriate for use with a nucleic acid amplification method also may be included. The components of the kit are packaged together in a common container, typically including instructions for performing selected specific embodiments of the methods disclosed herein.

EXAMPLES

Example 1

Design of SDA Primer Sets

A portion of the vly gene for GV has been sequenced and characterized for targeting by amplification assays. For purpose of this assay, a portion of the GV genome (i.e. the vly gene) that had not previously been targeted for amplification assays was selected. This sub-region of the GV genome was analyzed in current GenBank database for GV specificity. The vly gene for GV is represented by SEQ ID NOs. 1, 2, and 23-25.

Amplification primers were designed to amplify GV target sequences as described in Table 1. The positions of the regions of the GV vly gene to which the selected oligonucleotides (amplification primers, bumper primers, and adapter oligonucleotides) anneal are illustrated in FIGS. 1, 3 and 4. One example of a set of SDA primers and probes is described in Table 4 below. The underlined portions of the primer/probe sequences represents the target binding sequences. Restriction endonuclease recognition sites (RERS) sites are in bold.

Target levels tested were 100, 50, 20, 5, 1 and 0 copies/reaction (c/rxn). Sample (159 µL) was added to the appropriate priming microwells.

TABLE 5

| Eluate | |
|---|---|
| Reagent | Concentration |
| KOH | 75.000 mM |
| Bicine | 125.500 mM |
| Glycerol | 8.550% |
| DMSO | 9.810% |
| Proclin | 0.015% |
| Tween-20 | 0.005% |

The microwell plates were transferred to a 72° C. heat block. The corresponding amplification microwell plates were placed on a 54° C. heat block. The microwells were then incubated for 10 minutes. Aliquots (100 uL) of the microwell contents from the priming reaction were transferred to the amplification microwell.

The contents of the amplification microwells were mixed 3×50 uL. The amplification microwells were sealed and the microwell plates were transferred into a BD ProbeTec™ ET instrument supplied by Becton Dickinson & Co. of Franklin Lakes, N.J.

TABLE 4

Primary Oligonucleotides of SDA Assays for Amplification and/or Detection of GV

| SEQ ID | Description | Oligonucleotides 5' Sequence 3' | ORF Location (bp)* |
|---|---|---|---|
| SEQ ID NO: 14 | Left Bumper (upstream) | GTA TAC CCA GGT GCT | 343-357 |
| SEQ ID NO: 15 | Left Amplification Primer (upstream) | ACC GCA TCG AAT GCA TGT CTC GGG AAT ATG CCA AGC CTG A | 388-403 |
| SEQ ID NO: 16 | Right Bumper (downstream) | GCG CTG AAC AGT TAC | 472-486 |
| SEQ ID NO: 17 | Right Amplification Primer (downstream) | CGA TTC CGC TCC AGA CTT CTC GGG GCA AAT CAA CGC TCA A | 430-445 |
| SEQ ID NO: 18 | Probe-vly/GV Gene (detector) | (6FAM) TCC CCG AG(dT-Dabcyl) GCA AAC CGC GCT CCA A | 409-424 |

*Accession No. EU522486

Example 2

Sensitivity Testing with Three Strains of GV

The sensitivity of the GV vly assay was determined by performing a limit of detection (LOD) experiment. Genomic DNA, isolated from three strains of GV, was tested and a LOD calculated for each strain. Twenty-four repetitions were run for each target level and data was analyzed using the LOD calculator from Becton Dickinson & Co. The data shows that the assay is both sensitive and specific for GV.

The DNA for all three strains was diluted in 9 mM Tris, 1 mM EDTA, pH 8.0 and boiled for five minutes and allowed to cool for 10 minutes. The DNA was diluted to appropriate working dilution in the eluate described in Table 5 below.

The final reaction conditions were:

TABLE 6

| Final SDA Reaction Conditions | |
|---|---|
| Reagent | [Final SDA Rxn] |
| KOH | 75.000 mM |
| Bicine | 125.500 mM |
| Glycerol | 8.550% |
| DMSO | 9.810% |
| Proclin | 0.015% |
| Tween-20 | 0.005% |
| KPO4 | 40.000 mM |
| Trehalose | 1.853% |

TABLE 6-continued

Final SDA Reaction Conditions

| Reagent | [Final SDA Rxn] |
|---------|-----------------|
| BSA | 0.1007 ug/uL |
| DTT | 0.360 mM |
| dATP | 0.100 mM |
| dGTP | 0.125 mM |
| dTTP | 0.125 mM |
| dCsTP | 0.125 mM |
| GV vly LB7 | 0.050 uM |
| GV vly LP6 | 0.100 uM |
| GV vly RP7 | 0.500 uM |
| GV vly RB8 | 0.050 uM |
| GV vly DT5 | 0.200 uM |
| Bst | 25.0 units |
| BsoBI | 62.0 units |
| MgOAc | 4.943 mM |

The calculated levels of detection (LOD) for each strain in a clean, non-extracted system, without extraneous human DNA, were:

TABLE 7

LOD

| Strain | LOD (c/rxn) | CI (c/rxn) |
|--------|-------------|------------|
| G. vaginalis 14018 | 40 | (36, 43) |
| G. vaginalis 14019 | 58 | (55, 61) |
| G. vaginalis 49145 | 19 | (18, 21) |

Note:
CI is the 95% confidence interval

The sensitivity of the GV vly assay is given in Table 7. This assay is capable of detecting the three strains of GV tested. The data indicates that the SDA assay described in the present invention can detect at least 58 *Gardnerella vaginalis* genomic copies per reaction, in which the 95% LOD would be 55 genomic copies per reaction.

Example 3

Cross-Reactivity Testing

A cross-reactivity screen was performed. Nucleic acids from thirty-four organisms were extracted and tested on the Viper XTR instrument. A negative result was obtained for each.

Organisms were grown in broth culture to 1 McFarland and quantified by direct plate count. Cell pellets were prepared by centrifuging aliquots of the broth culture to harvest the cells. After discarding the supernatant, cell pellets were stored at $-70°$ C. For this experiment, cell pellets were resuspended in 1 mL sample diluent. After processing on the Viper XTR instrument, each sample was tested at approximately $2 \times 10^7$ CFU/reaction. The organisms listed in Table 9 were tested at that concentration, with two exceptions. *T. vaginalis* was grown in broth culture, quantified by direct count, and tested at $2 \times 10^5$ cells/reaction. *C. trachomatis* was cultured in BGMK cells, harvested by sonication and differential centrifugation and quantified by immunocytochemistry. *C. trachomatis* was tested at $5 \times 10^6$ EB/reaction. Positive control samples were prepared by diluting GV genomic DNA to a concentration of 1000 copies/mL for use as a positive control. Unspiked sample diluent (Table 8) was used as a negative control.

TABLE 8

Sample Diluent

| Reagent | Concentration |
|---------|---------------|
| Bis Tris Propane | 10 mM |
| $KPO_4$ | 15 mM |
| Triton X-100 | 2% |
| Sodium dodecyl sulfate | 1% |

The sample racks were pre-warmed at 114° C. for 15 minutes, then cooled at room temperature for 15 minutes. The prepared samples were transferred to the Viper™ XTR instrument from Becton Dickinson & Co. of Franklin Lakes, N.J. for extraction and analysis. In the Viper XTR system, nucleic acids are extracted from the samples using magnetic particles. Magnetic particle separation removes non-nucleic acid constituents of the sample. The nucleic acid is then eluted from the magnetic particles using the solution described in Table 5. The eluate was then tested using SDA, with probe sets described in Table 4 above.

The cross reactivity panel included the organisms in Table 9. The results demonstrate that the only organisms detected were the GV positive controls. No other organisms were detected, which demonstrated that the SDA primer probe set described above in Table 4 has very low cross-reactivity with other organisms.

TABLE 9

Cross Reactivity Test Results

| Organism | ID | Test Result[1] |
|----------|-----|----------------|
| Acinetobacter lwoffi | ATCC 19001 | Negative |
| Alcaligenes faecalis | ATCC 8750 | Negative |
| Bifidobacterium breve | ATCC 15700 | Negative |
| Bifidobacterium dentium | ATCC 27534 | Negative |
| Chlamydia trachomatis (H) | ATCC VR-879 | Negative |
| Chlamydia trachomatis (LGV2) | ATCC VR-902B | Negative |
| Clostridium perfringes | ATCC 13124 | Negative |
| Cryptococcus neoformans | ATCC 36556 | Negative |
| Enterbacter cloacae | ATCC 13047 | Negative |
| Entercoccus faecalis | ATCC 29212 | Negative |
| Entercoccus faecium | ATCC 19434 | Negative |
| Escherichia coli (strain K1) | ATCC 700973 | Negative |
| Gamella haemolysans | ATCC 10379 | Negative |
| Haemophilius ducreyi | ATCC 33940 | Negative |
| Haemophilius influenzae | ATCC 33533 | Negative |
| Kingella kingae | ATCC 23330 | Negative |
| Klebsiella pneumoniae | ATCC 13883 | Negative |
| Lactobacillus acidophilius | ATCC 4356 | Negative |
| Lactobacillus iners | ATCC 55195 | Negative |
| Lactibacillius jensenii | ANR 3670 | Negative |
| Mobiluncus mulieris | ATCC 35239 | Negative |
| Moraxella lacunata | ATCC 17967 | Negative |
| Mycoplasma genitalium | ATCC 33530 | Negative |
| Neisseria gonorrhoeae | ATCC 19424 | Negative |
| Neisseria meningitides | ATCC 13077 | Negative |
| Peptostrepococcus productus | ATCC 27340 | Negative |
| Propionibacterium acnes | ATCC 6919 | Negative |
| Pseudomonas aeruginosa | ATCC 27853 | Negative |
| Salmonella typhimurium | ATCC 13311 | Negative |
| Staphylcoccus aureus | ATCC 25923 | Negative |
| Staphylococcus epidermidis | E155 | Negative |
| Streptococcus agalactiae | ATCC 12386 | Negative |
| Streptococcus pneumoniae | ATCC 6303 | Negative |
| Trichomonas vaginalis | ATCC 30001 | Negative |

[1] Per GNE algorithm

| Control Samples | Test Result |
|---|---|
| G. vaginalis gDNA Positive Control | Positive |
| G. vaginalis gDNA Positive Control | Positive |
| G. vaginalis gDNA Positive Control | Positive |
| G. vaginalis gDNA Positive Control | Positive |
| Negative (no template) control | Negative |
| Negative (no template) control | Negative |
| Negative (no template) control | Negative |
| Negative (no template) control | Negative |

Example 4

Additional Cross-Reactivity Testing Against Six Species of Candida

In a clinical setting, it is important for the clinician to be able to differentiate between bacterial vaginosis and vaginal candidiasis. To demonstrate the utility of the GV SDA assay to do so, the assay was evaluated with genomic DNA from six medically relevant species of Candida. The GV SDA assay did not cross-react with any of the Candida species tested. Specifically, genomic DNA from six species of Candida was tested in the GV vly assay described in Example 1 above. Six replicates for each target were run.

The species of organisms used are enumerated in Table 10 below:

TABLE 10

| Organism Species | |
|---|---|
| Organism | ID |
| GV genomic DNA (gDNA) | ATCC 49145 |
| C. albicans | ATCC 11006 |
| C. kefyr | ATCC 66028 |
| C. tropicalis | ATCC 750 |
| C. krusei | ATCC 6258 |
| C. glabrata | ATCC 2001 |
| C. parapsilosis | ATCC 22019 |

The DNA was diluted in 10 mM Tris, 1 mM EDTA, pH 8.0 and boiled for five minutes. The solution was allowed to cool for ten minutes. The DNA was then diluted using the eluate described in Table 5. Sample (159 µL) was added to the appropriate priming microwells. The microwell plates were transferred to a 72° C. heat block. The corresponding amplification microwell plates were placed on a 54° C. heat block. The microwells were then incubated for 10 minutes. Aliquots (100 uL) of the microwell contents from the priming reaction were transferred to the amplification microwell. The amplification microwells were sealed and the microwell plates were transferred into BD ProbeTec ET instrument supplied by Becton Dickinson & Co. of Franklin Lakes, N.J.

REFERENCE CITED AND EQUIVALENTS

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for detecting a *Gardnerella vaginalis* (GV) target sequence if present in a sample comprising:
   (a) providing at least one oligonucleotide primer that will anneal to at least some portion of a target region of the vly gene of GV selected from the group consisting of SEQ ID NO. 20 and SEQ ID NO. 21;
   (b) combining the at least one oligonucleotide primer with a biological sample;
   (c) subjecting the sample to conditions to cause amplification of a portion of the target sequence, if present, in the sample; and
   (d) determining the presence or absence of the amplified target sequence.

2. The method of claim 1 wherein at least one oligonucleotide primer has a target binding sequence that is selected from one of SEQ ID NO. 3-13, complements of SEQ ID NO. 3-13 and sequences that share at least 70% sequence similarity with SEQ ID NO. 3-13 and complements thereof.

3. The method of claim 1 wherein at least one oligonucleotide primer has a target binding sequence that is selected from one of SEQ ID NO. 3-13, complements of SEQ ID NO. 3-13 and sequences that share at least 80% sequence similarity with SEQ ID NO. 3-13 and complements thereof.

4. The method of claim 1 wherein at least one oligonucleotide primer has a target binding sequence that is selected from one of SEQ ID NO. 3 to 13, complements of SEQ ID NO. 3-13 and sequences that share at least 90% sequence similarity with SEQ ID NO. 3 to 13 and complements thereof.

5. The method of claim 1 wherein the at least one oligonucleotide primer is a set of oligonucleotide primers wherein:
   (a) the first amplification primer has a target binding sequence that consists essentially of SEQ ID NO: 3, 6, 8 or 11; and
   (b) the second amplification primer has a target that consists essentially of binding sequence of SEQ ID NO: 4, 7, 9 or 12.

6. The method of claim 1 wherein said amplification is accomplished by an amplification reaction that is selected from the group consisting of a Strand Displacement Amplification (SDA) reaction and a Polymerase Chain Reaction (PCR).

7. The method of claim 1 wherein said amplification is accomplished by an amplification or detection reaction that is selected from the group consisting of direct detection, polymerase chain reaction (PCR), in situ hybridization, transcription mediated amplification (TMA), self sustained sequence replication (SSR) rolling circle amplification or nucleic acid sequence based amplification (NASBA).

8. The method of claim 1 wherein the amplification primer further comprises a hairpin, G-quartet, restriction site or a sequence which hybridizes to a reporter probe.

9. The method of claim 1 wherein the reporter probe further comprises a detectable label.

10. The method of claim 9 wherein the label is a fluorescent label.

11. The method of claim 1 wherein the amplification primer further comprises a restriction endonuclease recognition site or a RNA polymerase promoter.

12. The method of claim 1 further comprising amplifying an internal amplification control (IAC).

13. A method for detecting a *Gardnerella vaginalis* (GV) target sequence comprising:
   (a) providing a biological sample;
   (b) combining one or more amplification primers for a target region of the vly gene of GV, wherein the target region of the vly gene of GV has a sequence selected from the group consisting of SEQ ID NO. 20 and SEQ ID NO. 21 with the biological sample;
   (c) subjecting the biological sample combined with the one or more amplification primers to conditions that cause the one or more amplification primers to hybridize to the target region of the vly gene of GV; and
   (d) determining the presence or absence of the hybridized amplification primer in the biological sample.

14. The method of claim 13 wherein the one or more amplification primers have a target binding sequence of any one of SEQ ID NOS: 3 to 13 and complements thereof, and sequences that share at least 70% sequence similarity with SEQ ID NO. 3 to 13 and complements thereof.

15. The method of claim 13 wherein the one or more amplification primers have a target binding sequence of any one of SEQ ID NOS: 3 to 13 and complements thereof, and sequences that share at least 80% sequence similarity with SEQ ID NO. 3 to 13 and complements thereof.

16. The method of claim 15 wherein the one or more amplification primers have a target binding sequence of any one of SEQ ID NOS: 3 to 13 and complements thereof, and sequences that share at least 90% sequence similarity with SEQ ID NO. 3 to 13 and complements thereof.

17. The method of claim 13 wherein at least one amplification primer is a reporter probe that further comprises a detectable label.

18. The method of claim 17 wherein said detectable label is TAMRA, 6ROX, or 6FAM.

* * * * *